(12) United States Patent
Piry et al.

(10) Patent No.: US 10,532,309 B2
(45) Date of Patent: Jan. 14, 2020

(54) ANTIMICROBIAL FILTER MEDIUM AND CABIN AIR FILTER

(71) Applicants: MANN+HUMMEL GmbH, Ludwigsburg (DE); NEENAH GESSNER GMBH, Bruckmuehl (DE)

(72) Inventors: Alexander Piry, St. Wendel (DE); Ralf Blum, Aham (DE); Ellen Fritz, Rosenheim (DE)

(73) Assignee: MANN+HUMMEL GmbH, Ludwigsburg (DE)

( * ) Notice: Subject to any disclaimer, the term of this patent is extended or adjusted under 35 U.S.C. 154(b) by 44 days.

(21) Appl. No.: 15/797,595

(22) Filed: Oct. 27, 2017

(65) Prior Publication Data
US 2018/0085697 A1    Mar. 29, 2018

Related U.S. Application Data

(63) Continuation of application No. 14/096,745, filed on Dec. 4, 2013, now abandoned, which is a continuation of application No. PCT/EP2012/060501, filed on Jun. 4, 2012.

(30) Foreign Application Priority Data

Jun. 6, 2011 (DE) .......................... 10 2011 104 628

(51) Int. Cl.
*A61L 9/16* (2006.01)
*B01D 46/00* (2006.01)

(52) U.S. Cl.
CPC ............ *B01D 46/0028* (2013.01); *A61L 9/16* (2013.01); *A61L 2209/14* (2013.01); *B01D 2239/0407* (2013.01); *B01D 2275/10* (2013.01)

(58) Field of Classification Search
CPC .. B01D 46/10; B01D 46/521; B01D 2279/60; B01D 39/1623; B01D 2275/10; B01D 46/2408; F02M 35/024; F02M 35/04; A61L 9/00; A61L 9/12; A61L 9/16; A61L 9/02
USPC ........ 55/385.3, 486; 96/222, 223; 123/198 E
See application file for complete search history.

(56) References Cited

U.S. PATENT DOCUMENTS

| | | | |
|---|---|---|---|
| 5,288,298 A | 2/1994 | Aston | |
| 5,869,073 A * | 2/1999 | Sawan | A01N 25/24 424/404 |
| 6,165,243 A | 12/2000 | Kawaguchi et al. | |
| 6,224,655 B1 | 5/2001 | Messier | |
| 6,387,141 B1 * | 5/2002 | Hollingsworth | B01D 39/1623 55/486 |
| 6,926,828 B2 * | 8/2005 | Shiraishi | B01D 35/30 210/310 |

(Continued)

FOREIGN PATENT DOCUMENTS

| | | |
|---|---|---|
| DE | 19950374 A1 | 4/2001 |
| DE | 102004060020 A1 | 6/2006 |

(Continued)

*Primary Examiner* — Minh Chau T Pham
(74) *Attorney, Agent, or Firm* — James Hasselbeck

(57) ABSTRACT

A filter medium with antimicrobial action and a cabin air filter for filtering air for the interior area of motor vehicles, having at least one first filter layer where pollutants can be retained, and a second filter layer adjacent to the first filter layer is provided. The second filter layer is attached to the on-flow side of the first filter layer and contains antimicrobial agents.

15 Claims, 4 Drawing Sheets

(56) References Cited

U.S. PATENT DOCUMENTS

| | | |
|---|---|---|
| 7,520,912 B2 | 4/2009 | Sakadume et al. |
| 2003/0094102 A1 | 5/2003 | Maeoka |
| 2003/0116022 A1 | 6/2003 | Kritzler |
| 2003/0116202 A1 | 6/2003 | Krishnamoorthy et al. |
| 2004/0211160 A1* | 10/2004 | Rammig .................. A47L 9/12 55/382 |
| 2005/0079379 A1 | 4/2005 | Wadsworth et al. |
| 2006/0021302 A1 | 2/2006 | Bernard |
| 2007/0181001 A1 | 8/2007 | Bohringer et al. |
| 2007/0261376 A1 | 11/2007 | Elliot et al. |
| 2008/0302713 A1 | 12/2008 | Patrick |
| 2008/0317802 A1* | 12/2008 | Lee ........................ A01N 43/80 424/409 |
| 2010/0269465 A1* | 10/2010 | Choi .................. B01D 39/1623 55/486 |
| 2010/0296966 A1 | 11/2010 | Bae |
| 2011/0113538 A1 | 5/2011 | Von Bluecher et al. |

FOREIGN PATENT DOCUMENTS

| | | |
|---|---|---|
| DE | 202007010383 U1 | 10/2007 |
| EP | 1882511 A2 | 1/2008 |
| GB | 2307425 A | 5/1997 |
| JP | H11235507 A | 8/1999 |
| JP | 2000005529 A | 1/2000 |
| JP | 2001213157 A | 8/2001 |
| JP | 2011000561 A | 1/2011 |
| WO | 2007043164 A1 | 4/2009 |

* cited by examiner

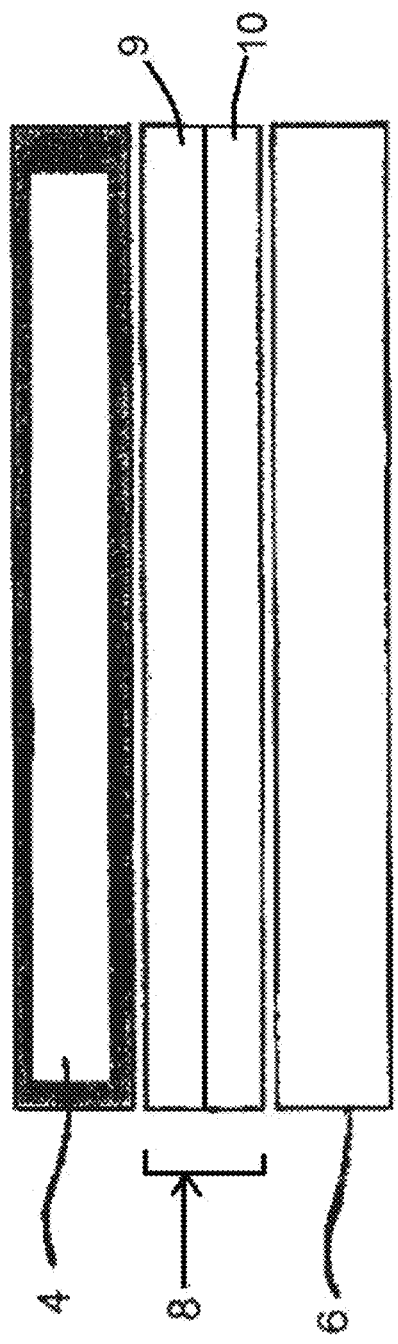
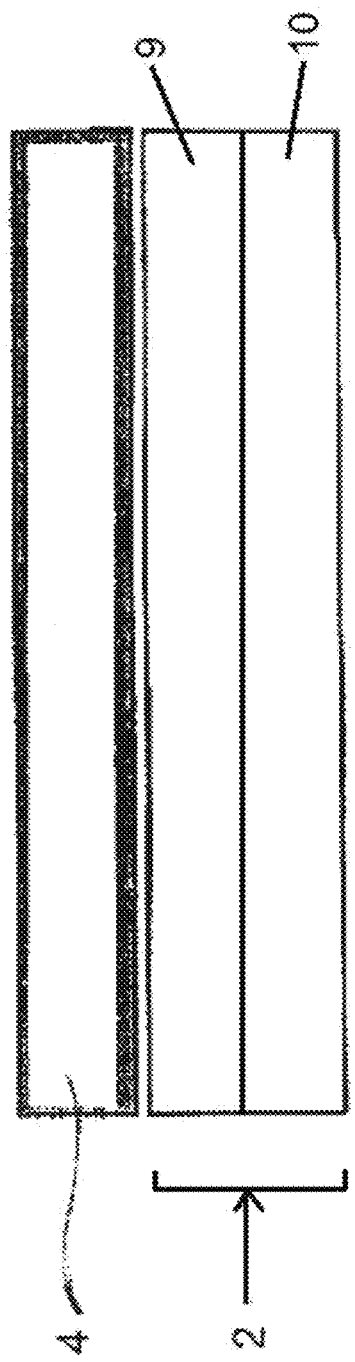

ANTIMICROBIAL FILTER MEDIUM AND CABIN AIR FILTER

CROSS REFERENCE TO RELATED APPLICATIONS

This application is a continuation application of U.S. application Ser. No. 14/096,745, filed Dec. 4, 2013, now abandon. The entire contents of the aforesaid U.S. application is incorporated herein by reference in its entirety. U.S. Ser. No. 14/096,745 is a continuation application of international application No. PCT/EP2012/060501 having an international filing date of Jun. 4, 2012 and designating the United States, the international application claiming a priority date of Jun. 6, 2011, based on prior filed German patent application No. 10 2011 104 628.7.

TECHNICAL FIELD

The present invention concerns generally a filter medium. In particular, it concerns a filter medium with antimicrobial action. Especially, it concerns a filter medium and a filter element comprising such a filter medium for filtering air for the cabin of a motor vehicle, i.e., a motor vehicle cabin filter. Moreover, the invention concerns a filter module.

BACKGROUND OF THE INVENTION

Filter elements produced from filter media serve for filtering fluid flows or gaseous media, for example, for filtering an air flow which is supplied to the vehicle cabin of a motor vehicle. Even though it is applicable to any type of filter elements, the present invention and problem to be solved by it will be described in the following in connection with a filter medium or filter element for filtering air for the cabin of a motor vehicle. In the following, such filters are referred to as motor vehicle cabin filters for short.

The increasing air pollution, in particular in big cities, in combination with the use of modern air conditioning systems makes it desirable and also necessary to filter by means of a suitable filter the air that is supplied from the exterior into the cabin of a motor vehicle and that is processed and air-conditioned. For this purpose, for example, particle filters or odor filters or alternatively also combinations thereof are conceivable which are to filter out the particles contained in the air as well as inherent odors from the ambient air as much as possible and to adsorb materials of the ambient air. Such filters for filtering air for the cabin of a motor vehicle are generally known in a plurality of embodiments and variants so that their configuration and function will only be briefly addressed in the following.

Since the efficiency of filters depends in particular on the size of the surface area of the filter that is flowed through by the air, for motor vehicle cabin filters primarily zigzag-shaped folded filter media are used that are also often referred to as pleated filter media. In this way, due to the folding of the employed filter medium, depending on the height of the folds and the fold spacing of the various fold sections of the filter medium, an effective enlargement of the filter surface area flowed through by the air flow can be provided.

As already mentioned, due to the increasing air pollution, increasingly more pollutants are present in the environment of a motor vehicle so that the motor vehicle cabin filter is exposed to an increasing load. These pollutants can be, for example, dust and soot particles as well as pollen, bacterial spores and fungal spores, bacteria and fungi. Some metabolic products of the microorganisms are known to constitute allergic substances for the human respiratory system. In some individuals, they can cause asthma attacks and it is proven that they can cause an immunological defense reaction.

U.S 2003/0 116 2022 A1 describes an air filter for air-conditioning systems as they are used in offices, apartment buildings and buildings for medical services such as hospitals and medical care homes. The filter comprises a composition that contains a biocide that is not bonded to the filter surface but is adapted such that it can migrate through the fine dust that is collecting on the filter so that the pollutant particles are coated with the biocide. Suitable biocides are, for example, 2-bromo-2-nitropropane-1,3-diol, isothiazoline compounds, benzoic acid, benzalkonium halides and the like.

U.S. 2006/0021302 A1 discloses an antimicrobial air filter whose filtration medium contains a "prophylactic" compound that can be used to reduce the number of microbial organisms. The "prophylactic" compound is introduced as a separate layer adjacent to the pleated filter medium. The "prophylactic" compound may be water-soluble coenzymes, oil-soluble coenzymes, plant extracts, antibiotics, biocidal metals, aliphatic and aromatic fatty acids, and the like.

WO 2006/003515 A1 discloses an air treatment device for a particle filter of an air conditioning device of a motor vehicle. The device is comprised of a permeable container that contains a volatile treatment agent. The container is attached to the particle filter.

U.S. 2005/0079379 A1 discloses a cover fabric with at least one fabric web that comprises an electrostatically charged meltblown fiber nonwoven nap that is treated with a fluorine chemical with a weak cationic emulsifying agent in order to reduce the surface energy of the fibers to thereby minimize penetration and wetting by oily mists and maintain thereby the effect of the electrostatic charges imparted to the fibers. The fibers can contain polyvinyl-N-pyridinium bromide. The fabric is used for face masks and protective clothing. Use in vehicle cabin filters is not proposed.

Finally, EP 1 882 511 A1 discloses a filter medium with bactericidal effect in particular for filtering air for the cabin of motor vehicles, comprised of at least one filter layer in which contaminants are retainable and a bactericidal filter layer which is downstream of this filter layer and is arranged on the clean air side of the at least one filter layer and is spaced by a spacer layer from the at least one filter layer.

A disadvantage of the solutions disclosed in the prior art is, on the one hand, that they cannot be applied easily to motor vehicle cabin filters and, on the other hand, that they cannot effectively prevent growth of microorganisms on the filter medium and in particular cannot prevent penetration of growth. Moreover, growth, in particular of fungi or fungal spores, is not prevented or only prevented to a minimal extent by the disclosed solutions. Some of the disclosed biocidal agents show an effectiveness only against certain microorganisms, for example, bacteria, but not against molds; for others, an effective inhibition of microbial growth is not ensured by the application of the biocides and the construction of the filter medium.

SUMMARY OF THE INVENTION

An object of the present invention is to provide a filter medium with antimicrobial action that avoids the aforementioned disadvantages of the prior art. Moreover, the present invention provides the possibility that an already existing filter medium can be furnished with an additional antimicrobial layer without the filtration efficiency being changed.

These and further objects are solved by a filter medium with antimicrobial action comprising a first filter layer in which contaminants can be retained and a second filter layer that contains antimicrobial substances and is adjacent to the first filter layer at the inflow side of the first filter layer.

The first filter layer can be a nonwoven, in particular a meltblown nonwoven.

Such a filter medium can be used in particular for filtering air for the cabin of motor vehicles. Other fields of use are however also conceivable, for example, in air conditioning devices for building services or also generally in filter systems, for example, in which a particle filter layer or a second filter layer is to be protected, in particular against microorganisms such as fungi or fungal spores, in particular molds or mold spores, bacteria or algae and in particular those in living, reproductive or propagating form.

As an antimicrobial agent, zinc pyrithione can be used in particular. Alternatively or additionally, octa-isothiazolone can be used as an antimicrobial agent. The second filter layer can contain additionally antimicrobial substances on the basis of nano silver. The second filter layer can additionally contain antimicrobial metals and metal compounds, in particular silver, copper and aluminum compounds and/or 2-bromo-2-nitropropane-1,3-diol, further isothiazoline compounds, benzoic acid and its derivatives, benzalkonium halides, water-soluble coenzymes, oil-soluble coenzymes, plant extracts, antibiotics, biocidal metals, aliphatic and/or aromatic fatty acids, and/or quaternary surfactants as antimicrobial substances.

The antimicrobial substances and/or additional biocidal substances can preferably be applied by spray application, slop padding or by means of a foulard machine.

The filter medium itself can be of a two-layer or three-layer configuration. In the sequence of through-flow, for example, a particle filter layer and an odor filter layer, comprising active carbon, may follow behind the antimicrobial layer. Alternatively, an odor filter layer and then a particle filter layer can follow behind the antimicrobial layer.

The antimicrobial substances or the additional bactericidal substances can be added directly when producing the second filter layer. Alternatively or in combination, the antimicrobial substances or the additional bactericidal substances can be introduced subsequently into the second filter layer.

Such a filter medium is in particular suitable for a motor vehicle cabin filter. In this connection, the filter medium is preferably folded or undulated for increasing the surface area. In different embodiments, the folded or undulated filter medium can be provided on at least one side with a lateral band of nonwoven or can be embedded by injection molding into a plastic frame. The folded or undulated filter medium can have at least at one of its terminal edges, these are the sides of the folded or undulated filter medium that have a zigzag or undulated shape, a lateral band, in particular a lateral band of nonwoven.

A motor vehicle cabin filter with the described medium can be used as an exchangeable filter element in a filter module, in particular the filter module of a motor vehicle air conditioning device, comprising a filter receptacle or a filter housing.

BRIEF DESCRIPTION OF THE DRAWINGS

The accompanying Figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Features of the present invention, which are believed to be novel, are set forth in the drawings and more particularly in the appended claims. The invention, together with the further objects and advantages thereof, may be best understood with reference to the following description, taken in conjunction with the accompanying drawings. The drawings show a form of the invention that is presently preferred; however, the invention is not limited to the precise arrangement shown in the drawings.

FIG. 1A schematically depicts a variant of the two-layer configuration of FIG. 1 in which the first filter layer under the antimicrobial second filter layer includes a particle filter layer and an odor filter layer;

FIG. 2A schematically depicts a variant of the three-layer configuration of FIG. 2 in which the first filter layer under the antimicrobial second filter layer includes a particle filter layer and an odor filter layer;

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

The medium according to the invention can be used, for example, in cabin filters for motor vehicles. Further fields of application are vacuum cleaner filters, filter elements for building and stationary air conditioning devices, filter elements for air purifiers, respiratory filters and the like.

In the following, the invention will be explained based on the example of a cabin air filter element for a motor vehicle. However, to a person of skill in the art it is readily apparent that the invention is not limited thereto but, as already mentioned above, can also be used in other fields.

The filter medium according to the invention is capable of killing microorganisms, in particular fungi or fungal spores, and at the same time of preventing effectively growth of bacteria, fungi, and other microorganisms on the filter medium and in particular of preventing effectively penetration of growth. The term penetration of growth means the propagation of mycel-forming microorganisms through a barrier layer, for example, a biocidal layer. This can also happen in connection with bacteria that propagate through this layer.

It is proposed according to the invention to design a filter medium with antimicrobial action in such a way that a second filter layer containing antimicrobial substances is mounted on the inflow side of a first filter layer that is adjacent to the second filter layer and that can retain contaminants. Accordingly, penetration of growth even of mycel-forming microorganisms is effectively prevented.

The mold spores are retained because of their size (2-100 μm, typically 2-10 μm) partially by the antimicrobial layer or impinge on the filter layer furnished with the antimicrobial substance and can therefore be inactivated or inhibited in their growth. This is the great advantage relative to a downstream antimicrobial filter layer because in this case the spores from the ambient air are retained mainly in the upstream particle layer and can germinate therein.

Figure 2:
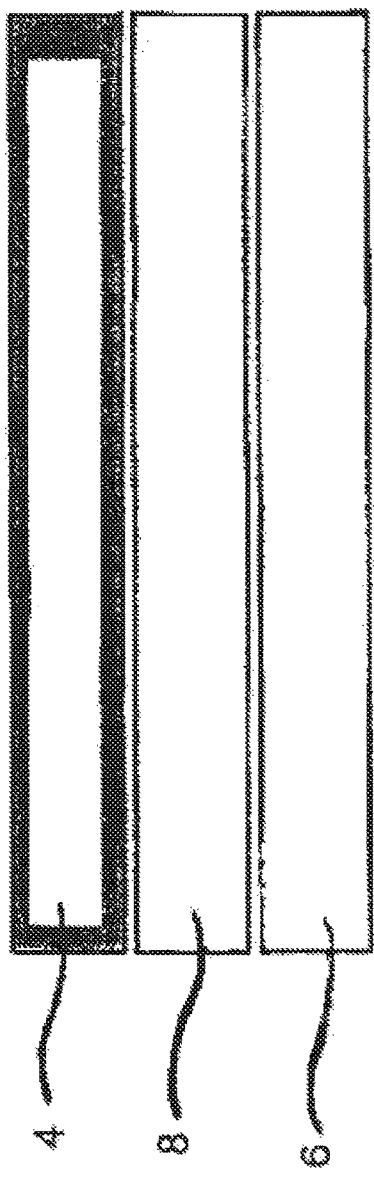
FIG. 2 schematically depicts a three-layer configuration of the filter medium according to the invention.
Figure 1:
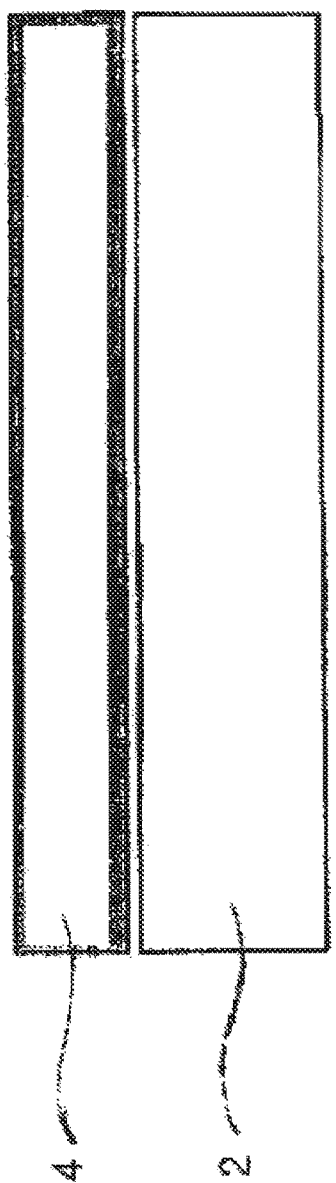
FIG. 1 schematically depicts a two-layer configuration of the filter medium according to the invention.
Figure 3:
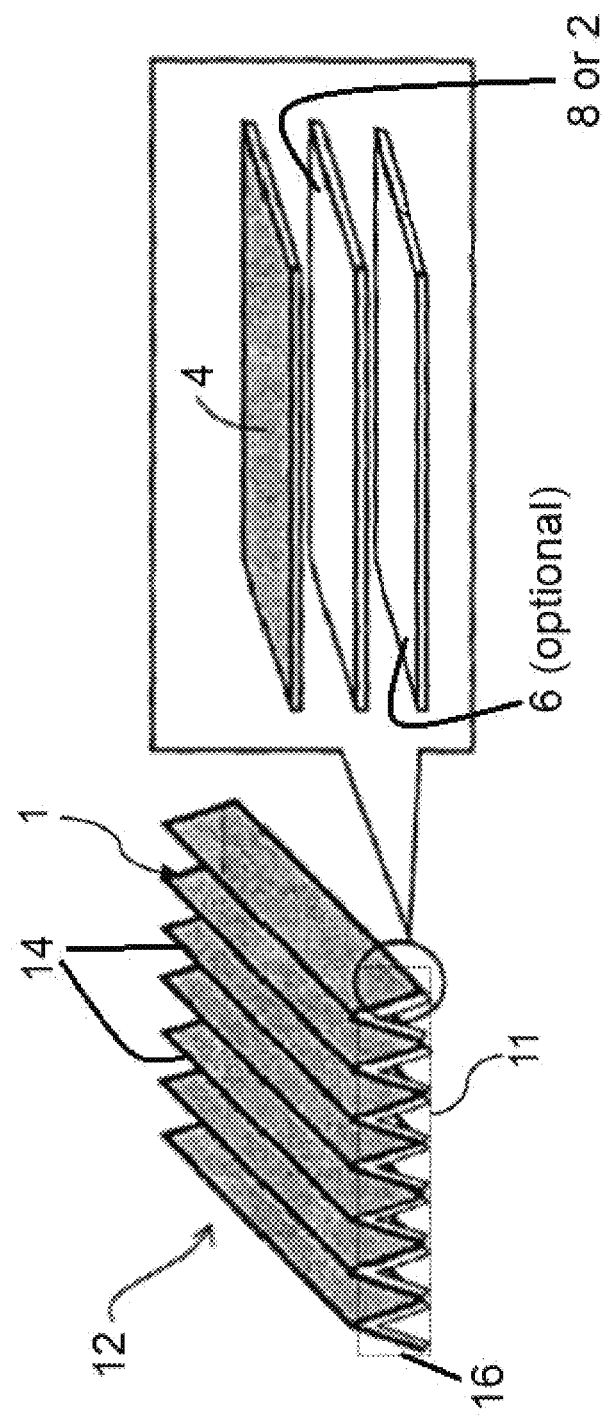
FIG. 3 schematically depicts a vehicle cabin filter, consistent with the present invention.
Figure 4:
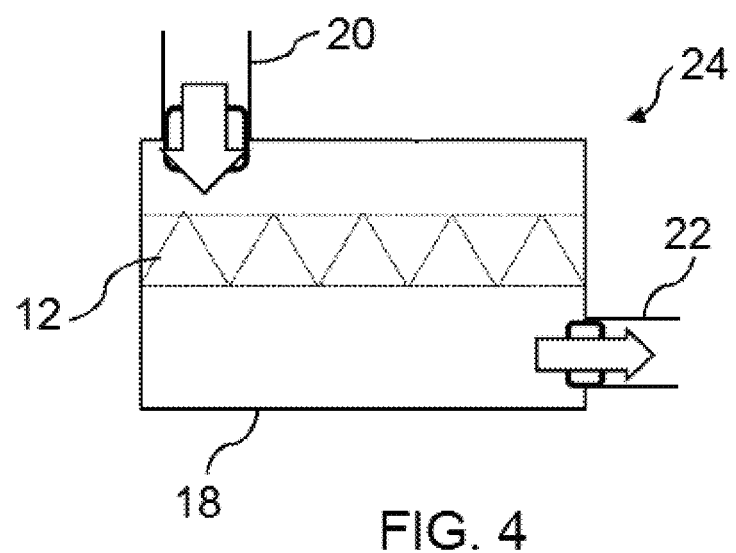
FIG. 4 schematically depicts the vehicle cabin filter installed into a filter receptacle or filter housing, consistent with the present invention.

The filter medium according to the invention is typically constructed such that the antimicrobial layer, i.e., the second filter layer comprising antimicrobial substances, is mounted as an additional layer (medium layer) on a medium. The antimicrobial layer has also a filter action and can optionally be used also as a single layer variant. In this context, the medium can either be designed of a two-layer or three-layer configuration. FIG. 1 shows a two-layer configuration of a particle filter medium 2 (first filter layer) and a second filter layer 4 applied thereon which contains antimicrobial substances. The first filter layer 2 can optionally have a graduated configuration, i.e., in cross-section in the flow direction can have a decreasing or increasing fiber diameter and/or can contain nanofibers that improve primarily the separating performance in regard to fine particles. FIG. 1A schematically depicts a variant of the two-layer configuration of FIG.1 in which the first filter layer 2 under the antimicrobial second filter layer 4 includes a particle filter layer 9 overlaid on an odor filter layer 10, preferably having activated carbon. FIG. 2 shows a three-layer configuration of a fine fiber layer 6 which has been produced, for example, according to the meltblown process, and a further fiber layer 8 that due to its mechanical strength is also referred to as a support and on which the second antimicrobial fiber layer 4 is applied. FIG. 2A schematically depicts a variant of the three-layer configuration of FIG. 2 in which the further fiber or support layer 8 includes a particle filter layer 9 overlaid on an odor filter layer 10, preferably having activated carbon. FIG. 3 schematically depicts a vehicle cabin filter 12 having the multi-layer filter medium described above, folded into peats 14 and having a lateral sideband 16. The folded or undulated filter medium can be provided on at least one side with a lateral band 16 of nonwoven or can be embedded by injection molding into a plastic frame. The folded or undulated filter medium can have at least at one of its terminal edges, these are the sides of the folded or undulated filter medium that have a zigzag or undulated shape, a lateral band 16, in particular a lateral band of nonwoven. FIG. 4 schematically depicts a filter arrangement 24 having the vehicle cabin filter 12 installed into a filter receptacle 18 or filter housing. Schematically depicted is an air inlet 20 and air outlet 22 of the filter receptacle 18 or filter housing.

The antimicrobial support can be provided with different microbial substances, for example, silver, copper, aluminum compounds. A particularly advantageous microbial substance is Zn pyrithione because it has a significant fungi-inhibiting effect and a very minimal solubility in water. A further preferred substance is octa-isothiazolone. Also, a finish on the basis of nano silver and enzymatically, chemically acting substances is possible, for example, 2-bromo-2-nitropropane-1,3-diol, isothiazoline compounds, benzoic acid and benzoic acid derivatives, benzalkonium halides, water-soluble and oil-soluble coenzymes, plant extracts, further biocidal metals, aliphatic and aromatic fatty acids, as well as quaternary surfactants, wherein the substances can be used as a further option as well as in combination with Zn pyrithione. Different grammages can be used for the second filter layer.

Furnishing the second filter layer with the antimicrobial or biocidal substances can be performed by means of different processes, for example, by spray application, slop padding or by means of a foulard machine. The antimicrobial layer is advantageously applied to the inflow side. Due to the afore described three-layer configuration, negative interactions between active substance and the functional particle fiber layer can be avoided in this way. Because of the special three-layer sandwich configuration, it is possible to protect the actual particle filter layer and to ensure in this way a high filtration efficiency. Also, the sandwich configuration has the advantage that in this way different filter media that can be used in cabin filters of motor vehicles can be furnished with an additional antimicrobial layer that can be offered as an additional option for the existing filters (in case of a motor vehicle cabin filters a plurality of different filter media are employed that are tailored to regional as well as manufacturer-specific requirements). Moreover, with the additional antimicrobial layer, tailored solutions for different fields of applications can be achieved. Also, for example, in different climatic conditions, different microorganisms play a role in connection with the growth on the filter medium so that the antimicrobial substances applied to the second filter layer can be selected appropriately and, in addition, the grammage can be varied.

In addition, the layer (meltblown) that determines the filtration efficiency can be finished in a master batch with antimicrobial substances or the medium can exhibit an increased antimicrobial action by means of additional introduction of antimicrobial fibers produced by a master batch.

The subsequent application of the substance in comparison to the addition directly during fiber manufacture (master batch) has the advantage that reduced substance concentrations are sufficient because the substance is externally present on the fiber and therefore is in direct contact with the microorganisms. An advantage of master batch production or addition of fibers produced by a master batch process resides in that the antimicrobial substances are anchored particularly strongly on the fiber.

The filter medium according to the invention can be used to produce a filter module, in particular a particle and/or odor filter, with a filter housing, wherein the filter medium is inserted into the filter housing.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The invention claimed is:

1. An antimicrobial cabin air filter of a motor vehicle, comprising:
   a multi-layer filter medium having:
      a first filter layer of nonwoven fibers operative to filter and retain contaminants removed from an airflow stream; and a second filter layer having antimicrobial substances,
wherein the filter medium is adapted to remove microbial contaminants from the airflow stream to a passenger cabin of the motor vehicle,
wherein the second filter layer is arranged to overlay the first filter layer;
wherein the second filter layer is attached onto and abutting against the first filter layer without interposing intermediate layers on an inflow side of the first filter layer;
wherein the antimicrobial substances include octa-isothiazolone;
wherein the antimicrobial substances additionally comprise at least one substance selected from the group consisting of: 2-bromo-2-nitropropane-1,3-diol, benzoic acid and its derivatives, and antibiotics;
wherein the antimicrobial substances are provided in the second filter layer rather than the first filter layer, avoiding interactions between the antimicrobial substances and the first filter layer to ensure a high filtration efficiency, and to inhibit growth of microorganisms on the first filter layer by treating the airflow stream before it reaches the first filter layer;
wherein the multi-layer filter medium is folded or undulatated into a plurality of pleats, forming a multi-layer pleated filter medium having a zigzag or undulated shape;
wherein terminal edges of the plurality of pleats are fixed to either:
a lateral band fixed onto and covering terminal edges of the plurality of pleats on at least one lateral side of the multi-layer pleated filter medium; or
the terminal edges are embedded into a plastic frame surrounding the pleated filter medium.

2. The antimicrobial cabin air filter according to claim 1, wherein
the first filter layer has a graduated configuration such that non-woven fibers decrease in fiber diameter a flow direction from the inflow side to an outflow side of the first filter layer.

3. The antimicrobial cabin air filter according to claim 1, wherein
the first filter layer comprises at least two layers:
a particle filter layer arranged at the inflow side of the first filter layer;
an odor filter layer having activated carbon arranged at an outflow side of the first filter layer;
wherein the particle filter layer is arranged overlaid directly on the odor filter layer.

4. The antimicrobial cabin air filter according to claim 2, wherein
the first filter layer has a graduated configuration such that non-woven fibers decrease in fiber diameter a flow direction from the inflow side to an outflow side of the first filter layer;
wherein the first filter layer comprises at least two layers:
a particle filter layer arranged at the inflow side of the first filter layer;
an odor filter layer having activated carbon arranged at an outflow side of the first filter layer;
wherein the particle filter layer is arranged overlaid directly on the odor filter layer.

5. The antimicrobial cabin air filter according to claim 1, wherein
the second filter layer further includes antimicrobial substances selected from the group consisting of: plant extracts, quaternary surfactants and aromatic fatty acids.

6. The antimicrobial cabin air filter according to claim 1, wherein
the second filter layer further includes antimicrobial metals of copper or compounds of copper.

7. The antimicrobial cabin air filter according to claim 1, wherein
the second filter layer additionally comprises benzalkonium halides.

8. The antimicrobial cabin air filter according to claim 1, wherein
the second filter layer additionally further includes at least one antimicrobial metals or metal compounds of aluminum compounds.

9. The antimicrobial cabin air filter according to claim 1, wherein the antimicrobial substances and/or additional biocidal substances are applied onto the second filter layer by spray application, slop padding or by means of a foulard machine.

10. The antimicrobial cabin air filter according to claim 1, wherein the filter medium further includes:
a fine fiber layer of meltblown fibers overlaid onto an outflow side of the first filter layer.

11. The antimicrobial cabin air filter according to claim 1, wherein
the antimicrobial substances or additional bactericidal substances are added to the second layer directly during manufacture of the second filter layer.

12. The antimicrobial cabin air filter according to claim 1, wherein
the antimicrobial substances or additional bactericidal substances are added into the second filter layer after manufacture of the second filter layer.

13. The antimicrobial cabin air filter according to claim 1, wherein
at least some of the antimicrobial substances are provided in a master batch from which fibers of the second filter layer are formed, such that the antimicrobial substances are incorporated directly in the fibers during manufacture rather than being introduced subsequently onto the second filter layer after fiber manufacture.

14. The antimicrobial cabin air filter according to claim 1, wherein
the second filter layer additionally further includes at least one antimicrobial metal or metal compound of aluminum.

15. A filter module of a motor vehicle cabin air conditioning device, comprising:
the antimicrobial cabin air filter according to claim 1;
a filter receptacle or a filter housing;
wherein the antimicrobial cabin air filter is arranged within the filter receptacle or filter housing.

* * * * *